United States Patent [19]
Baker

[11] Patent Number: 5,840,920
[45] Date of Patent: Nov. 24, 1998

[54] PROCESS FOR PREPARING COMPOSITIONS USEFUL AS INTERMEDIATES FOR PREPARING LUBRICATING OIL AND FUEL ADDITIVES

[75] Inventor: Mark R. Baker, Lyndhurst, Ohio

[73] Assignee: The Lubrizol Corporation, Wickliffe, Ohio

[21] Appl. No.: 694,046

[22] Filed: Aug. 8, 1996

[51] Int. Cl.$^6$ .................. C07D 313/00; C07D 307/02
[52] U.S. Cl. ................ 549/266; 549/273; 549/295; 549/320
[58] Field of Search .................. 549/266, 273, 549/295, 320

[56] References Cited

U.S. PATENT DOCUMENTS

| | | | |
|---|---|---|---|
| 3,172,892 | 3/1965 | Le Suer et al. | 260/326.5 |
| 3,215,707 | 11/1965 | Rense | 260/326.3 |
| 3,454,607 | 7/1969 | Le Suer et al. | 260/408 |
| 3,954,808 | 5/1976 | Elliott et al. | 260/343.2 R |
| 3,966,807 | 6/1976 | Elliott et al. | 260/559 D |
| 4,046,802 | 9/1977 | Elliott et al. | 560/61 G |
| 4,051,049 | 9/1977 | Elliott et al. | 252/51.5 A |
| 4,083,791 | 4/1978 | Elliott et al. | 252/51.5 A |
| 4,108,784 | 8/1978 | Bryant | 252/56 R |
| 4,194,886 | 3/1980 | Ripple | 44/70 |
| 4,205,960 | 6/1980 | Bryant | 44/68 |
| 4,234,435 | 11/1980 | Meinhardt et al. | 252/51.5 A |
| 4,285,824 | 8/1981 | Bryant | 252/56 |
| 4,412,031 | 10/1983 | Kitahara et al. | 524/526 |
| 4,412,041 | 10/1983 | Kitahara et al. | 525/154 |
| 4,525,541 | 6/1985 | Kitahara et al. | 525/337 |
| 4,654,435 | 3/1987 | Kitahara et al. | 560/61 |
| 4,704,427 | 11/1987 | Kitahara et al. | 524/531 |
| 5,137,980 | 8/1992 | DeGonia et al. | 252/327.6 |
| 5,336,278 | 8/1994 | Adams et al. | 44/419 |
| 5,458,793 | 10/1995 | Adams et al. | 252/47 |
| 5,739,356 | 4/1998 | Dietz et al. | 549/285 |

FOREIGN PATENT DOCUMENTS

| | | |
|---|---|---|
| 0331556A2 | 6/1989 | European Pat. Off. . |
| 95/31488 | 11/1995 | WIPO . |

OTHER PUBLICATIONS

B.B. Jarvis et al., Synthesis, 11, 1079 (1990).
K. Mikami et al., Chem. Rev. 92, 1021 (1992).
M. Terada et al., Tetrahedron Letters, 35, 6693 (1994).
D. Savostianoff, C.R. Acad. Sc. Paris, 263, 605 (Aug. 22, 1966).

*Primary Examiner*—Amelia Owens
*Attorney, Agent, or Firm*—Joseph P. Fischer; James L. Cordek

[57] ABSTRACT

A process for reacting olefinic compounds, certain carboxylic reactants, and aldehydes or ketones and products prepared by the process. The compositions of the process are useful as intermediates for the preparation of additives for lubricants and fuels.

21 Claims, No Drawings

PROCESS FOR PREPARING COMPOSITIONS USEFUL AS INTERMEDIATES FOR PREPARING LUBRICATING OIL AND FUEL ADDITIVES

FIELD OF THE INVENTION

This invention relates to a process for preparing compositions which are useful as intermediates for the preparation of low chlorine containing additives for lubricating oils and normally liquid fuels, compounds prepared by the process, and coupled lactone compounds.

BACKGROUND OF THE INVENTION

Numerous types of additives are used to improve lubricating oil and fuel compositions. Such additives include, but are certainly not limited to dispersants and detergents of the ashless and ash-containing variety, oxidation inhibitors, anti-wear additives, friction modifiers, and the like. Such materials are well known in the art and are described in many publications, for example, Smalheer, et al, "Lubricant Additives", Lezius-Hiles Co., Cleveland, Ohio, USA (1967); M. W. Ranney, Ed., "Lubricant Additives", Noyes Data Corp., Park Ridge, N.J. USA (1973); M. J. Satriana, Ed., "Synthetic Oils and Lubricant Additives, Advances since 1979, Noyes Data Corp., Park Ridge N.J. USA (1982), W. C. Gergel, "Lubricant Additive Chemistry", Publication 694-320-65R1 of The Lubrizol Corp., Wickliffe, Ohio, USA (1994); and W. C. Gergel et al, "Lubrication Theory and Practice" Publication 794-320-59R3 of The Lubrizol Corp., Wickliffe, Ohio, USA (1994); and in numerous United States patents, for example Chamberlin, III, U.S. Pat. No. 4,326,972, Schroeck et al, U.S. Pat. No. 4,904,401, and Ripple et al, U.S. Pat. No. 4,981,602. Many such additives are frequently derived from carboxylic reactants, for example, acids, esters, anhydrides, lactones, and others. Specific examples of commonly used carboxylic compounds used as intermediates for preparing lubricating oil additives include alkyl-and alkenyl substituted succinic acids and anhydrides, polyolefin substituted carboxylic acids, aromatic acids, such as salicylic acids, and others. Illustrative carboxylic compounds are described in Meinhardt, et al, U.S. Pat. No. 4,234,435; Norman et al, U.S. Pat. No. 3,172,892; LeSuer et al, U.S. Pat. No. 3,454,607, and Rense, U.S. Pat. No. 3,215,707.

Many carboxylic intermediates used in the preparation of lubricating oil additives contain chlorine. While the amount of chlorine present is often only a very small amount of the total weight of the intermediate, the chlorine frequently is carried over into the carboxylic derivative which is desired as an additive. For a variety of reasons, including government regulation, environmental concerns, and commercial reasons the industry has been making efforts to reduce or to eliminate chlorine from additives designed for use as lubricant or fuel additives.

Accordingly, it is desirable to provide low chlorine or chlorine free intermediates which can be used to prepare low chlorine or chlorine free derivatives for use in lubricants and fuels.

The present invention provides a method for preparing compounds which meet this requirement.

B. B. Snider and J. W. van Straten, J. Org. Chem., 44, 3567–3571 (1979) describes certain products prepared by the reaction of methyl glyoxylate with several butenes and cyclohexenes. K. Mikami and M. Shimizu, Chem. Rev., 92, 1021–1050 (1992) describe carbonyl-ene reactions, including glyoxylate-ene reactions. D. Savostianov (communicated by P.Pascal), C. R. Acad. Sc. Paris, 263, (605–7) (1966) relates to preparation of some α-hydroxylactones via the action of glyoxylic acid on olefins. M. Kerfanto et. al., C. R. Acad. Sc. Paris, 264, (232–5) (1967) relates to condensation reactions of α-α-di-(N-morpholino)-acetic acid and glyoxylic acid with olefins.

SUMMARY OF THE INVENTION

The present invention relates to a process for preparing compounds useful as intermediates for preparing performance improving additives for lubricants and fuels which comprises reacting, optionally in the presence of an acidic catalyst selected from the group consisting of organic sulfonic acids, heteropolyacids, and mineral acids, (A) at least one olefinic compound of the general formula

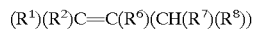

wherein each of $R^1$ and $R^2$ is, independently, hydrogen or a hydrocarbon based group and each of $R^6$, $R^7$ and $R^8$ is, independently, hydrogen or a hydrocarbon based group;

(B) at least one carboxylic reactant selected from the group consisting of compounds of the formula $$R^3C(O)(R^4)_nC(O)OR^5 \qquad (IV)$$

and compounds of the formula

wherein each of $R^3$, $R^5$ and each $R^9$ is independently H or a hydrocarbyl group, $R^4$ is a divalent hydrocarbylene group, and n is 0 or 1 in amounts ranging from 0.6 moles (B) per mole of (A) to 1.5 moles (B) per equivalent of (A); and from about 0.5 to about 2 moles, per mole of (B), of (C) at least one aldehyde or ketone; as well as products obtained by the process of the invention.

DETAILED DESCRIPTION OF THE PREFERRED EMBODIMENTS

As used herein, the terms "hydrocarbon", "hydrocarbyl" or "hydrocarbon based" mean that the group being described has predominantly hydrocarbon character within the context of this invention. These include groups that are purely hydrocarbon in nature, that is, they contain only carbon and hydrogen. They may also include groups containing non-hydrocarbon substituents or atoms which do not alter the predominantly hydrocarbon character of the group. Such substituents may include alkoxy-, nitro-, etc. These groups also may contain hetero atoms. Suitable hetero atoms will be apparent to those skilled in the art and include, for example, sulfur, nitrogen and oxygen. Therefore, while remaining predominantly hydrocarbon in character within the context of this invention, these groups may contain atoms other than carbon present in a chain or ring otherwise composed of carbon atoms.

In general, no more than about three non-hydrocarbon substituents or heteroatoms, and preferably no more than one, will be present for every 10 carbon atoms in the hydrocarbon, hydrocarbyl or hydrocarbon based groups. Most preferably, the groups are purely hydrocarbon in nature, that is they are essentially free of atoms other than carbon and hydrogen.

Throughout the specification and claims the expression soluble or dispersible is used. By soluble or dispersible is meant that an amount needed to provide the desired level of activity or performance can be incorporated by being dissolved, dispersed or suspended in an oil of lubricating viscosity or in a normally liquid fuel. Usually, this means that at least about 0.001 % by weight of the material can be incorporated in a lubricating oil or normally liquid fuel. For a further discussion of the terms oil soluble and dispersible, particularly "stably dispersible", see U.S. Pat. No. 4,320,019 which is expressly incorporated herein by reference for relevant teachings in this regard.

As noted hereinabove, provided by this invention is a process for preparing low chlorine or chlorine free compositions useful as intermediates for preparing low chlorine or chlorine free additives for lubricating oil and fuel compositions.

The Process

In one embodiment, the present invention relates to a process comprising reacting, optionally in the presence of an acidic catalyst selected from the group consisting of organic sulfonic acids, heteropolyacids, and mineral acids, (A) at least one olefinic compound of the general formula

wherein each of $R^1$ and $R^2$ is, independently, hydrogen or a hydrocarbon based group and each of $R^6$, $R^7$ and $R^8$ is, independently, hydrogen or a hydrocarbon based group (B) at least one carboxylic reactant selected from the group consisting of compounds of the formula

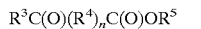   (IV)

and compounds of the formula

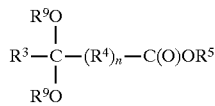   (V)

wherein each of $R^3$, $R^5$ and each $R^9$ is independently H or a hydrocarbyl group, $R^4$ is a divalent hydrocarbylene group, and n is 0 or 1 in amounts ranging from 0.6 moles (B) per mole of (A) to 1.5 moles (B) per equivalent of (A); and from about 0.5 to about 2 moles, per mole of (B), of (C) at least one aldehyde or ketone.

Reactants (A), (B), and (C) may be present at the outset of the reaction or (A) and (B) may be reacted first followed by reaction with (C). Under these conditions, all of (A) and (B) may be present at the same time; however, it has been found that improvements in yield and purity of the product arising from the reaction of (A) and (B) may be attained when the carboxylic reactant (B) is added to the olefinic compound (A) either portionwise or continuously over an extended period of time, usually up to about 10 hours, more often from 1 hour up to about 6 hours, frequently from about 2 to about 4 hours.

The process may be conducted in the presence of an azeotroping solvent. Well known azeotroping solvents include toluene, xylene, cyclohexane, etc. Cyclohexane is preferred.

The Catalyst

The first step of the process of this invention is optionally conducted in the presence of an acidic catalyst. Acid catalysts, such as organic sulfonic acids, for example, para-toluene sulfonic acid, methane sulfonic acid and sulfonated polymers such as those marketed under the tradename AMBERLYST® (Rohm & Haas), heteropolyacids, the complex acids of heavy metals (e.g., Mo, W, Sn, V, Zr, etc.) with phosphoric acids (e.g., phosphomolybdic acid), and mineral acids, for example, $H_2SO_4$ and phosphoric acid, are useful. The amount of catalyst used is generally small, ranging from about 0.01 mole % to about 10 mole %, more often from about 0.1 mole % to about 2 mole %, based on moles of olefinic reactant.

(A) The Olefinic Compound

The olefinic compound employed as a reactant in the process of this invention contains at least one group of the formula

   (I)

and has the general formula

   (III)

wherein each of $R^1$ and $R^2$ is, independently, hydrogen or a hydrocarbon based group. Each of $R^6$, $R^7$ and $R^8$ is, independently, hydrogen or a hydrocarbon based group; preferably at least one is a hydrocarbon based group containing at least 7 carbon atoms. These olefinic compounds are diverse in nature.

Virtually any compound containing an olefinic bond may be used provided it meets the general requirements set forth hereinabove for (III) and does not contain any functional groups (e.g., primary or secondary amines) that would interfere with the carboxylic reactant (B). Useful olefinic compounds may be terminal olefins, i.e., olefins having a $H_2C\!\!=\!\!C$ group, or internal olefins. Useful olefinic compounds may have more than one olefinic bond, i.e., they may be dienes, trienes, etc. Most often they are mono-olefinic. Examples include linear α-olefins, cis- or trans- disubstituted olefins, trisubstituted olefins and tetrasubstituted olefins.

When (A) is a monoolefinic, one mole of (A) contains one equivalent of C=C; when (A) is diolefinic, one mole of (A) contains 2 equivalents of C=C bonds; when (A) is triolefinic, one mole of (A) contains 3 equivalents of C=C bonds, and so forth.

Aromatic double bonds are not considered to be olefinic double bonds within the context of this invention.

As used herein, the expression "polyolefin" defines a polymer derived from olefins. The expression "polyolefinic" refers to a compound containing more than one C=C bond.

Among useful compounds are those that are purely hydrocarbon, i.e., those substantially free of non-hydrocarbon groups, or they may contain one or more non-hydrocarbon groups or atoms as discussed in greater detail herein.

In one embodiment, the olefinic compounds are substantially hydrocarbon, that is, each R group in (III) is H or contains essentially carbon and hydrogen. In one aspect within this embodiment, each of $R^1$, $R^2$, $R^7$ and R8 is hydrogen and $R^6$ is a hydrocarbyl group containing from 7 to about 5,000 carbon atoms, more often from about 30 up to about 200 carbon atoms, preferably from about 50 up to about 100 carbon atoms. In another aspect of this embodiment, each of $R^1$ and $R^2$ is hydrogen, $R^6$ is H or a lower alkyl group, usually methyl, and the group $(CH(R^7)(R^8))$ is a hydrocarbyl group containing from 7 to about 5,000 carbon atoms, more typically from about 30 up to about 200 carbon atom, preferably from 50 up to about 100 carbon atoms.

As used here, and throughout the specification and claims, the expression "lower" with "alkyl", "alkenyl", etc. means groups having 7 or fewer carbon atoms, for example, methyl, ethyl and all isomers of propyl, butyl, pentyl, hexyl and heptyl, ethylene, butylene, etc.

In another embodiment, one or more of the R groups present in (III) is an organic radical which is not purely hydrocarbon. Such groups may contain or may be groups such as carboxylic acid, ester, amide, salt, including ammonium, amine and metal salts, cyano, hydroxy, thiol, tertiary amino, nitro, alkali metal mercapto and the like. Illustrative of olefinic compounds (III) containing such groups are methyl oleate, oleic acid, 2-dodecenedioic acid, octene diol, linoleic acid and esters thereof, and the like.

Preferably, the hydrocarbyl groups are aliphatic groups. In one preferred embodiment, when an R group is an aliphatic group containing a total of from about 30 to about 200 carbon atoms, the olefinic compound is derived from homopolymerized and interpolymerized $C_{2-18}$ mono- and di-olefins, preferably 1-olefins. In a preferred embodiment, the olefins contain from 2 to about 5 carbon atoms, preferably 3 or 4 carbon atoms. Examples of such olefins are ethylene, propylene, butene-1, isobutylene, butadiene, isoprene, 1-hexene, 1-octene, etc. R groups can, however, be derived from other sources, such as monomeric high molecular weight alkenes (e.g. 1-tetracontene), aliphatic petroleum fractions, particularly paraffin waxes and cracked analogs thereof, white oils, synthetic alkenes such as those produced by the Ziegler-Natta process (e.g., poly-(ethylene) greases) and other sources known to those skilled in the art. Any unsaturation in the R groups may be reduced by hydrogenation according to procedures known in the art, provided at least one olefinic group remains as described for (III).

In one preferred embodiment, at least one R is derived from polybutene, that is, polymers of $C_4$ olefins, including 1-butene, 2-butene and isobutylene. Those derived from isobutylene, i.e., polyisobutylenes, are especially preferred. In another preferred embodiment, R is derived from polypropylene. In another preferred embodiment, R is derived from ethylene-alpha olefin polymers, including ethylene-propylene-diene polymers. Representative of such polymers are the ethylene-propylene copolymers and ethylene-propylene-diene terpolymers marketed under the TRILENE® tradename by the Uniroyal Company. Molecular weights of such polymers may vary over a wide range, but especially preferred are those having number average molecular weights ($\overline{M}_n$) ranging from about 300 to about 20,000, preferably 700 to about 10,000, often from 900 to 2,500. In one preferred embodiment, the olefin is an ethylene-propylene-diene terpolymer having $\overline{M}_n$ ranging from about 900 to about 8,000, often up to about 2,000. Such materials are included among the TRILENE® polymers marketed by the Uniroyal Company, Middlebury, Conn. USA and ORTHOLEUM® 2052 marketed by the DuPont Company.

Ethylene-alpha olefin copolymers and ethylene-lower olefin-diene terpolymers are described in numerous patent documents, including European patent publication EP 279, 863, Japanese patent publication 87-129,303 and the following United States patents:

U.S. Pat. No. 3,598,738
U.S. Pat. No. 4,026,809
U.S. Pat. No. 4,032,700
U.S. Pat. No. 4,137,185
U.S. Pat. No. 4,156,061
U.S. Pat. No. 4,320,019
U.S. Pat. No. 4,357,250
U.S. Pat. No. 4,668,078
U.S. Pat. No. 4,668,834
U.S. Pat. No. 4,937,299
U.S. Pat. No. 5,324,800 each of which is incorporated herein by reference for relevant disclosures of these ethylene based polymers A preferred source of hydrocarbyl groups R are polybutenes obtained by polymerization of a $C_4$ refinery stream having a butene content of 35 to 75 weight percent and isobutylene content of 15 to 60 weight percent in the presence of a Lewis acid catalyst such as aluminum trichloride or boron trifluoride. These polybutenes contain predominantly (greater than 80% of total repeating units) isobutylene repeating units of the configuration

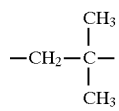

These polybutenes are typically monoolefinic, that is they contain but one olefinic bond per molecule.

The olefinic compound may be a polyolefin comprising a mixture of isomers wherein from about 50 percent to about 65 percent are tri-substituted olefins wherein one substituent contains from 2 to about 5000 carbon atoms, often from about 30 to about 200 carbon atoms, more often from about 50 to about 100 carbon atoms, usually aliphatic carbon atoms, and the other two substituents are lower alkyl.

When the olefin is a tri-substituted olefin, it frequently comprises a mixture of cis- and trans- 1-lower alkyl, 1-(aliphatic hydrocarbyl containing from 30 to about 100 carbon atoms), 2-lower alkyl ethene and 1,1-di-lower alkyl, 2-(aliphatic hydrocarbyl containing from 30 to about 100 carbon atoms) ethene.

In one embodiment, the monoolefinic groups are predominantly vinylidene groups, i.e., groups of the formula

especially those of the formula

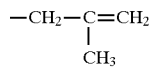

although the polybutenes may also comprise other olefinic configurations.

In one embodiment the polybutene is substantially monoolefinic, comprising at least about 30 mole %, preferably at least about 50 mole % vinylidene groups, more often at least about 70 mole % vinylidene groups. Such materials and methods for preparing them are described in U.S. Pat. Nos. 5,071,919; 5,137,978; 5,137,980; 5,286,823 and 5,408, 018, and in published European patent application EP 646103-A1, each of which is expressly incorporated herein by reference. They are commercially available, for example under the tradenames ULTRAVIS® (BP Chemicals) and Glissopal (BASF).

Illustrative is a polyolefin comprising a mixture of isomers, at least about 50% by weight of the mixture comprising isomers of the formula $H_2C=C(R^6)(CH(R^7)(R^8))$ wherein $R^6$ is H or lower alkyl, preferably methyl.

As is apparent from the foregoing, olefins of a wide variety of type and molecular weight are useful for preparing the compositions of this invention. Useful olefins are usually substantially hydrocarbon and have number average molecular weight ranging from about 100 to about 70,000, more often from about 200 to about 7,000, even more often from about 1,300 to about 5,000, frequently from about 400 to about 3,000. Lower olefins such as those containing from about 7 to about 30 carbon atoms, for example, octenes, octadecenes, mixed olefin, such as $C_{8-28}$ linear olefins, are useful.

Specific characterization of olefin reactants (A) used in the processes of this invention can be accomplished by using techniques known to those skilled in the art. These techniques include general qualitative analysis by infrared and determinations of average molecular weight, e.g., $\overline{M}_n$, number average molecular weight, and $\overline{M}_w$, weight average molecular weight, etc. employing vapor phase osmometry (VPO) and gel permeation chromatography (GPC). Structural details can be elucidated employing proton and carbon 13 ($C^{13}$) nuclear magnetic resonance (NMR) techniques. NMR is useful for determining substitution characteristics about olefinic bonds, and provides some details regarding the nature of the substituents. More specific details regarding substituents about the olefinic bonds can be obtained by cleaving the substituents from the olefin by, for example, ozonolysis, then analyzing the cleaved products, also by NMR, GPC, VPO, and by infra-red analysis and other techniques known to the skilled person.

(B) The Carboxylic Reactant

The carboxylic reactant is at least one member selected from the group consisting of compounds of the formula $$R^3C(O)(R^4)_nC(O)OR^5 \tag{IV}$$

and compounds of the formula $$\begin{array}{c} R^9O \\ | \\ R^3-C-(R^4)_n-C(O)OR^5 \\ | \\ R^9O \end{array} \tag{V}$$

wherein each of $R^3$, $R^5$ and each $R^9$ is independently H or a hydrocarbyl group.

$R^3$ is usually H or an aliphatic group, that is, alkyl or alkenyl, preferably alkyl, more preferably lower alkyl. Especially preferred is where $R^3$ is H or methyl, most preferably, H.

$R^4$ is a divalent hydrocarbylene group. This group may be aliphatic or aromatic, but is usually aliphatic. Often, $R^4$ is an alkylene group containing from 1 to about 3 carbon atoms. The 'n' is 0 or 1; that is, in one embodiment $R^4$ is present and in another embodiment, $R^4$ is absent. More often, $R^4$ is absent.

When $R^5$ is hydrocarbyl, it is usually an aliphatic group, often a group containing from 1 to about 30 carbon atoms, often from 8 to about 18 carbon atoms. In another embodiment, $R^5$ is lower alkyl, wherein "lower alkyl" is defined hereinabove, especially from 1 to 4 carbon atoms. Most often, $R^5$ is H or lower alkyl.

$R^9$ is usually H or alkyl, preferably H or lower alkyl.

Examples of carboxylic reactants (B) are glyoxylic acid, and other omega- oxoalkanoic acids, keto alkanoic acids such as pyruvic acid, levulinic acid, ketovaleric acids, ketobutyric acids, the hemiacetals, for example glyoxylic acid methyl ester methyl hemiacetal, and hemiketals thereof, and the corresponding acetals and ketals, and numerous others. The skilled worker, having the disclosure before him, will readily recognize the appropriate compound of formula (IV) and (V) to employ as a reactant to generate a given compound.

Reactant (B) may be a compound of the formula $$\begin{array}{c} HO \\ | \\ R^3-C-(R^4)_n-C(O)OR^5 \\ | \\ HO \end{array} \tag{VII}$$

wherein each of $R^3$ and $R^5$ is independently H or alkyl. Such compounds arise when reactant (B) is hydrated. Glyoxylic acid monohydrate is a representative example.

(C) The Aldehyde or Ketone

The aldehyde or ketone reactant employed in the process of this invention is a carbonyl compound other than a carboxy-substituted carbonyl compound. Accordingly, it is to be understood that it is not contemplated herein that reactant (C) includes any of the species defined hereinabove as reactant (B). Suitable compounds include those having the general formula RC(O)R', wherein R and R' are each, independently, H or a hydrocarbyl group as defined hereinabove. As noted in the description, hydrocarbyl groups may contain other groups or heteroatoms which do not interfere with the process and products of this invention. Preferably, reactant (C) contains from 1 to about 12 carbon atoms. Suitable aldehydes include formaldehyde, acetaldehyde, propionaldehyde, butyraldehyde, isobutyraldehyde, pentanal, hexanal, heptaldehyde, octanal, benzaldehyde, and higher aldehydes. Other aldehydes, such as dialdehydes, especially glyoxal, are useful, although monoaldehydes are generally preferred.

The most preferred aldehyde is formaldehyde, which can be supplied as the aqueous solution often referred to as formalin, but is more often used in the polymeric form as paraformaldehyde, which is a reactive equivalent of, or a source of, formaldehyde. Other reactive equivalents include hydrates or cyclic trimers.

Suitable ketones include acetone, butanone, methyl ethyl ketone, and other ketones. Preferably, one of the hydrocarbyl groups is methyl.

Mixtures of two or more aldehydes and/or ketones are also useful.

The process of this invention is conducted at temperatures ranging from ambient up to the lowest decomposition temperature of any of the reactants, usually from about 60° C. to about 220° C., more often from about 120° C. to about 180° C., preferably up to about 160° C. When the reaction is conducted in the presence of organic sulfonic acid or mineral acid catalyst, the reaction is usually conducted at temperatures up to about 160° C. The process employs from about 0.6 moles of reactant (B) per mole of olefinic compound (A), up to 1.5 moles (B) per equivalent of (A), more often from about 0.8 moles (B) per mole of (A) to about 1.2 moles (B) per equivalent of (A), even more often from about 0.95 moles (B) per mole of (A) to about 1.05 moles (B) per equivalent of (A). Reactant (C) is used in amounts ranging from about 0.5 to about 2 moles per mole of (B), preferably, from about 0.8 to about 1.5 moles per mole of (B), and most often from about 0.9 to about 1.1 moles per mole of (B). As noted herein, many reactants contain water which is removed. Removal of water at moderate temperatures is attainable employing reduced pressure, a solvent that aids in azeotropic distillation of water, or by purging with an inert gas such as $N_2$.

The progress of the reaction can be followed by observing the infra-red spectrum. The absorption for —COOH carbonyl of the products appears at about 1710 cm$^{-1}$. The total acid number as measured using essentially the procedure in ASTM D-664 (Potentiometric Method) or ASTM D-974 (Color Indicator Method) is useful together with the infrared, keeping in mind that non-acidic products (e.g., polyester products), those derived from non-acidic reactants and condensation products such as lactones will not display significant acid numbers.

These procedures appear in the Annual Book of ASTM Standards, Volume 05.01, ASTM, 1916 Race Street, Philadelphia, Pa. USA.

As noted hereinabove, products obtained by the process of this invention are provided. While it appears that the product obtained by the process of this invention is a fairly complex mixture, the mixture is believed to comprise at least one composition comprising a compound of the formula

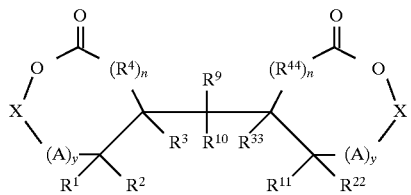

wherein each n=0 or 1; each y=0 or 1;

wherein each X is independently a divalent hydrocarbon based group selected from the group consisting of

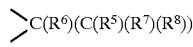

when y=0, and

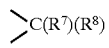

when y=1 wherein each of $R^1$, $R^{11}$, $R^2$, $R^{22}$, $R^3$ and $R^{33}$ is independently H or a hydrocarbon based group, preferably H or lower alkyl or alkenyl; each of $R^4$ and $R^{44}$ is a divalent hydrocarbylene group, preferably alkylene, more preferably containing 1 to about 3 carbon atoms; each A is a group of the formula

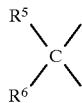

each $R^5$ is independently H or a hydrocarbon based group, preferably H or lower alkyl;

each of $R^6$, $R^7$, and $R^8$ is independently H or a hydrocarbon based group, preferably at least one being a hydrocarbon based group containing at least 7 carbon atoms, preferably from 7 to about 5000 carbon atoms; and each of $R^9$ and $R^{10}$ is independently H or a hydrocarbon based group, preferably H.

In one preferred embodiment, each of $R^1$, $R^{11}$, $R^2$, $R^{22}$, $R^3$ and $R^{33}$ is H and n=0. Especially preferred is where each of $R^1$, $R^{11}$, $R^2$, $R^{22}$ is independently H or lower alkyl.

In one embodiment, at least one of $R^6$ is an aliphatic group containing from about 10 to about 300 carbon atoms, especially those derived from a polymer selected from the group consisting of homopolymerized ant interpolymerized $C_{2-18}$ olefins, especially 1-olefins. The 1-olefins are preferably ethylene, propylene, butenes, isobutylene and mixtures thereof.

In still another embodiment, $R^6$ is an aliphatic group containing from 8 to about 24 carbon atoms; in another embodiment, from 12 to about 50 carbon atoms.

In one embodiment, X is the group

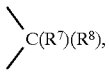

wherein at least one of $R^7$ and $R^8$ is an aliphatic group containing 10–300 carbon atoms, more often from about 30 to about 100 carbon atoms.

In yet another embodiment, at least one of $R^7$ and $R^8$ is an aliphatic group containing from 8 to about 24 carbon atoms; in another embodiment, from 12 to about 50 carbon atoms.

The following examples are intended to illustrate several compositions of this invention as well as means for preparing same. Unless indicated otherwise all parts are parts by weight, filtrations are conducted employing a diatomaceous earth filter aid, and analytical values are by actual analysis. The abbreviations GPC and VPO refer to gel permeation chromatography and vapor phase osmometry, respectively, both procedures being used to determine molecular weight. The abbreviation TLC-FID refers to thin layer chromatography using a flame ionization detector. Saponification numbers are determined using ASTM Procedure D-94. It is to be understood that these examples are not intended to limit the scope of the invention.

EXAMPLE 1

A reactor is charged with 250 parts of polyisobutylene (GLISSOPAL® ES3250, BASF) having $\overline{M}_n$ about 1000 and containing about 87 mole percent terminal vinylidene groups, 52 parts 50% aqueous glyoxylic acid, 15 parts paraformaldehyde and 1 part 70% aqueous methanesulfonic acid. These are heated with mixing, under $N_2$, to 160° C. and are held at temperature for a total of 4.5 hours. The materials are stripped to 135° C. and 25 millimeters Hg pressure (mm Hg) and filtered. The filtrate has saponification no =32.4, and contains (GPC) 96.3% material having $\overline{M}_n$=1432 and $\overline{M}_w$=2157.

EXAMPLE 2

A reactor is charged with 250 parts of the polyisobutylene of Example 1, 37 parts of 50% aqueous glyoxylic acid, 7.5 parts paraformaldehyde and 1 part 70% aqueous methanesulfonic acid. The materials are heated with mixing under $N_2$, to 160° C. and are held at temperature for 5 hours, collecting 26 parts water. The materials are stripped to 125° C. and 25 mm Hg and filtered. The filtrate has saponification no =40.3, contains 13.9% unreacted polyisobutylene and has (GPC) $\overline{M}_n$=1539 and $\overline{M}_w$=2693.

EXAMPLE 3

Employing the same reactants as in Example 2, 1200 parts of polyisobutylene, 177.6 parts 50% aqueous glyoxylic acid, 4.8 parts 70% aqueous methanesulfonic acid and 36 parts paraformaldehyde are reacted, under $N_2$, at 160° C. for 5.5 hours, collecting 114 parts water. The materials are cooled to 100° C. and stripped to 140° C. and 20 mm Hg and filtered. The filtrate has saponification no =44 and has (VPO) $\overline{M}_n$=1852.

EXAMPLE 4

Employing the same reactants as in Example 2, 3000 parts of polyisobutylene, 444 parts, 444 parts 50% aqueous glyoxylic acid, 12 parts 70% aqueous methanesulfonic acid and 99 parts paraformaldehyde are reacted, under $N_2$ at 160° C. for 5 hours, collecting 344 parts water then for an additional 3 hours. The materials are cooled then stripped to 160° C. and 30 mm Hg and filtered. The filtrate has saponification no =44, has (GPC) $\overline{M}_n$=1450 and contains 17% unreacted polyisobutylene.

EXAMPLE 5

Employing the same reactants as in Example 2, 3000 parts of polyisobutylene, 488 parts 50% aqueous glyoxylic acid, 12 parts 70% aqueous methanesulfonic acid and 99 parts paraformaldehyde are reacted, under $N_2$, at 120° C. for hours, collecting water then at 160° C. for 5 hours, collecting water. The materials are cooled to 140° C. and filtered. The filtrate has saponification no =50, has (GPC) $\overline{M}_n$=1475, $\overline{M}_w$=2422 and contains 15 % unreacted polyisobutylene.

EXAMPLE 6

A reactor is charged with 832 parts of polyisobutylene (GLISSOPAL ES3252) having $\overline{M}_n$ about 2400 and containing about 70 mole percent terminal vinylidene groups, 61.6 parts 50% aqueous glyoxylic acid, 13.7 parts paraformaldehyde, 3 parts 70% aqueous methanesulfonic acid, and 571.2 parts mineral oil. The materials are heated to 120° C. over 1 hour, collecting water, then to 160° C. over 1 hour, reacted at 160° C. for 8 hours, while collecting water. The materials are stripped to 160° C. and 25 mm Hg and filtered at 140° C. The filtrate has saponification no =13.4. (GPC) $\overline{M}_n$=4324, $\overline{M}_w$=9779 (65 %) and $\overline{M}_n$=340, $\overline{M}_w$=412. (35%).

EXAMPLE 7

A reactor is charged with 4000 parts polyisobutylene (ULTRAVIS® 10, BP Chemicals) having $\overline{M}_n$ about 1000 and containing about 80 mole % terminal vinylidene groups, 592 parts 50% aqueous glyoxylic acid, 132 parts paraformaldehyde and 16 parts 70% aqueous methanesulfonic acid. The materials are heated to 120° C. over 0.75 hour then to 160° C. over 2.5 hours, collecting water, then reacted at 160° C for a total of 6 hours; total water collected, 475 parts. The materials are stripped to 160° C. and 40 mm Hg and filtered. The filtrate contains 19.9% unreacted polyisobutylene, has saponification no. =42 and (GPC) $\overline{M}_n$=1419, $\overline{M}_w$=3272.

EXAMPLE 8

The procedure of Example 2 is repeated replacing the glyoxylic acid with an equivalent amount of pyruvic acid.

EXAMPLE 9

The procedure of Example 4 is repeated replacing glyoxylic acid with an equivalent amount of levulinic acid.

EXAMPLE 10

The procedure of Example 1 is repeated replacing glyoxylic acid with an equivalent amount of glyoxylic acid methyl ester methyl hemiacetal.

EXAMPLE 11

The procedure of Example 4 is repeated replacing glyoxylic acid with an equivalent amount of glyoxylic acid methyl ester methyl hemiacetal.

EXAMPLE 12

A reactor is charged with 1000 parts of the polyisobutylene used in Example 1, 148 parts of 50% aqueous glyoxylic acid, 29 parts glyoxal and 2 parts 70% aqueous methane sulfonic acid. Under $N_2$, the materials are heated to 130° C., held at 130° C. for 2 hours, heated to 160° C., and held at 160° C. for 4 hours, while collecting a total of 108 parts aqueous distillate. The materials are mixed with 730.7 parts mineral oil and filtered at 140° C. obtaining a filtrate having total acid no =11.8 and saponification no =26.5.

EXAMPLE 13

A reactor is charged with 800 parts of the polyisobutylene used in Example 1, 118.4 parts of 50% aqueous glyoxylic acid, 18.6 parts glyoxal and 1.6 parts 70% aqueous methane sulfonic acid. Under $N_2$, the materials are heated to 140° C., held at 140°–148° C. for 6 hours, then at 145° C. for 7 hours, while collecting aqueous distillate. The materials are mixed with 567 parts mineral oil and filtered at 145° C. obtaining a filtrate having total acid no =0, saponification no =23.2 and (GPC) 59.94% $\overline{M}_n$=1743, $\overline{M}_w$=2184; 40.1% $\overline{M}_n$=358.

EXAMPLE 14

A reactor is charged with 1000 parts of the polyisobutylene used in Example 1, 37 parts 50% aqueous glyoxylic acid, 35.6 parts nonyl aldehyde and 1 part 70% aqueous methane sulfonic acid. The materials are heated, under $N_2$, to 160° C. and are held at 160° C. for 5 hours while collecting 23.9 parts aqueous distillate. The materials are stripped to 125° C. at 56 mm Hg, then filtered at 20° C. The filtrate has total acid no. =14.8, saponification no. =36.4 and, by GPC, 100% $\overline{M}_n$ 1191, $\overline{M}_w$ 1881, and contains 25% unreated polyisobutylene (TLC-FID).

EXAMPLE 15

The procedure of Example 1 is repeated replacing the paraformaldehyde with 29 parts acetone.

EXAMPLE 16

The procedure of Example 6 is repeated replacing paraformaldehyde with 58 parts 2-octanone.

EXAMPLE 17

The procedure of Example 7 is repeated replacing paraformaldehyde with 729 parts benzophenone.

While the invention has been explained in relation to its preferred embodiments, it is to be understood that various modifications thereof will become apparent to those skilled in the art upon reading the specification. Therefore, it is to be understood that the invention disclosed herein is intended to cover such modifications that fall within the scope of the appended claims.

What is claimed is:

1. A composition comprising a compound of the formula

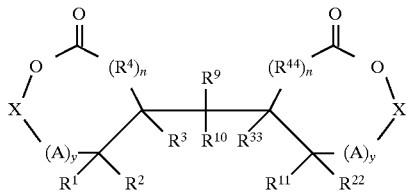

wherein each n=0 or 1; each y=0 or 1;

wherein each X is independently a divalent hydrocarbon based group selected from the group consisting of

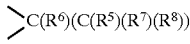

when y=0, and

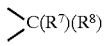

when y=1 wherein each of $R^1$, $R^{11}$, $R^2$, and $R^{22}$ is independently H or a hydrocarbon based group;

each of $R^3$ and $R^{33}$ is independently H or a hydrocarbon based group:

each of $R^4$ and $R^{44}$ is a divalent hydrocarbylene group;

each A is a group of the formula

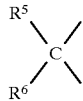

each $R^5$ is independently H or a hydrocarbon based group;
each of $R^6$, $R^7$, and $R^8$ is independently H or a hydrocarbon based group; and
each of $R^9$ and $R^{10}$ is independently H or a hydrocarbon based group.

2. The composition of claim 1 wherein at least one of $R^6$, $R^7$, and $R^8$ is a hydrocarbon based group containing at least 7 carbon atoms.

3. The composition of claim 1 wherein each of $R^1$, $R^{11}$, $R^2$, $R^{22}$, $R^3$, and $R^{33}$ is independently H and n=0.

4. The composition of claim 1 wherein each of $R^4$ and $R^{44}$ is an alkylene group containing from 1 to about 3 carbon atoms.

5. The composition of claim 1 wherein each of $R^1$, $R^{11}$, $R^2$, $R^{22}$, $R^3$, and $R^{33}$ is independently H and n=zero.

6. The composition of claim 1 wherein each X has the formula.

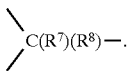

7. The composition of claim 1 wherein each X has the formula.

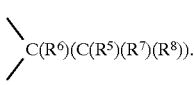

8. The composition of claim 7 wherein at least one of $R^6$, $R^7$, and $R^8$ is a hydrocarbon based group containing from about 7 to about 5000 carbon atoms.

9. The composition of claim 7 wherein at least one $R^6$ is an aliphatic group containing from about 10 to about 300 carbon atoms.

10. The composition of claim 9 wherein each $R^6$ contains from 30 to about 100 carbon atoms and is derived from a polymer selected from the group consisting of homopolymerized and interpolymerized $C_{2-18}$ olefins.

11. The composition of claim 6 wherein at least one of $R^7$ and $R^8$ is an aliphatic group containing from about 10 to about 300 carbon atoms.

12. The composition of claim 11 wherein at least one of $R^7$ and $R^8$ contains from about 30 to about 100 carbon atoms and is derived from a polymer selected from the group consisting of homopolymerized and interpolymerized $C_{2-18}$ olefins.

13. The composition of claim 10 wherein the olefins are 1-olefins.

14. The composition of claim 13 wherein the 1-olefins are ethylene, propylene, butenes, isobutylene and mixtures thereof.

15. The composition of claim 1 wherein at least one of $R^7$ and $R^8$ is an aliphatic group containing from 8 to about 24 carbon atoms.

16. The composition of claim 1 wherein at least one of $R^7$ and $R^8$ contains from 12 to about 50 carbon atoms.

17. The composition of claim 7 wherein $R^6$ is an aliphatic group containing from 8 to about 24 carbon atoms.

18. The composition of claim 7 wherein $R^6$ contains from 12 to about 50 carbon atoms.

19. The composition of claim 1 wherein each of $R^1$, $R^{11}$, $R^2$ and $R^{22}$ is independently H or lower alkyl.

20. The composition of claim 1 wherein $R^5$ is H or a lower alkyl group.

21. The composition of claim 1 wherein each of $R^9$ and $R^{10}$ is H.

* * * * *